United States Patent [19]

Ermert et al.

[11] Patent Number: 4,922,916

[45] Date of Patent: May 8, 1990

[54] MEDICAL EXAMINATION INSTALLATION WITH IMPROVED IMAGE CONTRAST

[75] Inventors: Helmut Ermert, Roettenbach; Manfred Pfeiler; Karl Barth, both of Erlangen, all of Fed. Rep. of Germany

[73] Assignee: Siemens Aktiengesellschaft, Berlin and Munich

[21] Appl. No.: 249,515

[22] Filed: Sep. 26, 1988

[30] Foreign Application Priority Data

Nov. 19, 1987 [DE] Fed. Rep. of Germany ....... 3739230

[51] Int. Cl.$^5$ .............................................. A61B 6/00
[52] U.S. Cl. ................................ 128/653 R; 358/111; 378/99
[58] Field of Search ................ 128/24 A, 328, 660.03, 128/653; 378/99; 358/111

[56] References Cited

U.S. PATENT DOCUMENTS 4,483,342  11/1984  Pfeifer .
4,709,385  11/1987  Pfeiler et al. .
4,741,008   4/1988  Franke ................... 128/328

FOREIGN PATENT DOCUMENTS 0168559  1/1986  European Pat. Off. ........... 128/328

*Primary Examiner*—Ruth S. Smith
*Attorney, Agent, or Firm*—Hill, Van Santen, Steadman & Simpson

[57] ABSTRACT

A medical examination installation for generating images of a patient for visual display has a mechanical oscillator which vibrates at least a portion of the patient, of which an image is to be obtained, during the exposure time. The image is obtained with a pick-up device at an image frequency, and the mechanical vibration may be matched to, or differ from, the image frequency. The image is then subjected to image subtraction techniques, or selective filtering, which permits body parts which differ in terms of mechanical vibration properties from the surrounding tissue, for example calculi, to be clearly imaged, particularly the borders of those body parts.

8 Claims, 1 Drawing Sheet

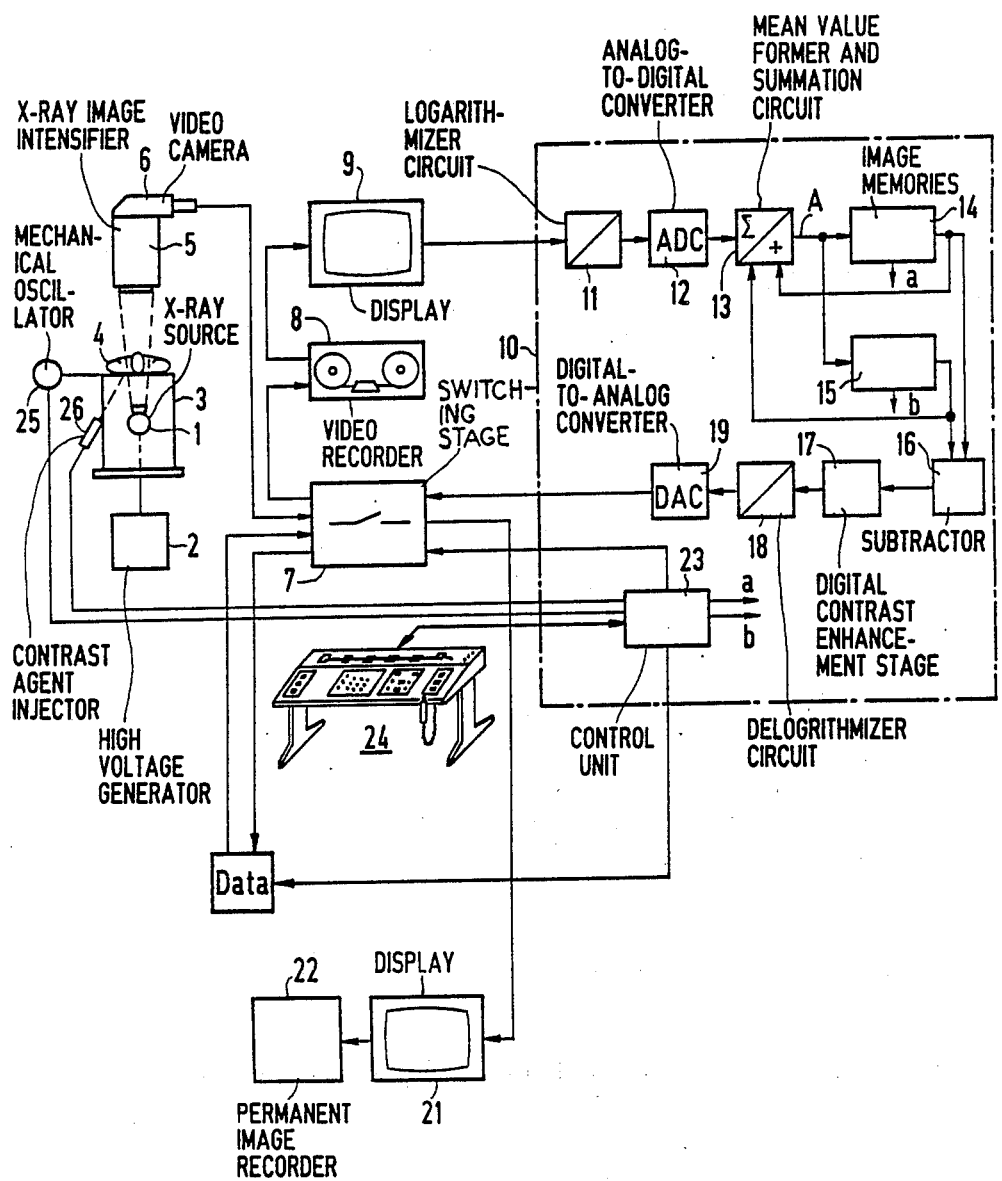

MEDICAL EXAMINATION INSTALLATION WITH IMPROVED IMAGE CONTRAST

BACKGROUND OF THE INVENTION

1. Field of the Invention

The present invention is directed to a medical examination installation for generating visual images of at least a portion of an examination subject, which uses an image pick-up system to obtain and process such images.

2. Related Application

The present application is related to an application having Ser. No. 249,516 entitled Medical Examination Installation With Improved Image Contrast, Ermert et al, filed simultaneously herewith.

3. Description of the Prior Art

Images of a body portion can be continuously produced with a medical examination installation, for example an x-ray installation. Body parts which exhibit only a slight contrast relative to neighboring tissue are inadequately represented in such images. For example, gallstones are frequently difficult to localize. It is required for modern therapy methods, for example lithotripsy, to be able to clearly visually display such body parts to that an exact positioning of the treatment instrument, such as a shock wave generator, can be achieved. Such exact placement is necessary, for example, for calculus disintegration.

SUMMARY OF THE INVENTION

It is an object of the present invention to provide an medical examination system wherein body parts having a low contrast relative to the surrounding tissue can be represented with an improved contrast.

The above object is achieved in accordance with the principles of the present invention in an examination installation wherein the portion of the patient to be examined is placed in mechanical vibration by a mechanical oscillator during the generation of an image of the patient. The image which is obtained of the patient is obtained via an image pick-up system operating at an image pick-up frequency. The frequency of the mechanical vibrations can be matched to, or differ from, the image pick-up frequency. As a result of the mechanical vibrations of the individual body parts, and the different mass moments of inertia of those body parts, the boundaries of the body parts, for example gallstones, are clearly portrayed using continuous image subtraction. It is thus easily possible to locate a calculus.

DESCRIPTION OF THE DRAWING

The single FIGURE is a schematic block diagram of a medical examination installation constructed in accordance with the principles of the present invention.

DESCRIPTION OF THE PREFERRED EMBODIMENTS

As shown in the drawing, a medical examination installation includes an x-ray tube 1 which is supplied by a high voltage generator 2, and generates x-rays which irradiate a patient 4 disposed on a patient support table 3. An image intensifier/video chain includes an x-ray image intensifier 5 with a video camera 6 attached thereto for recording the x-ray images and converting them into a video signal which is supplied to a switching stage 7. The switching stage 7 functions as a video signal distributor, and, depending upon the setting thereof, permits the signals corresponding to the x-ray images to be recorded on a video recorder 8 and supplied to a television monitor 9.

For generating differential images, the video signals in real time, or from the video recorder 8, are supplied to an image subtraction stage 10. The image subtraction stage 10 has a logarithmizer 11 which forms the input of the stage. The output signal of the logarithmizer 11 is supplied to an analog-to-digital converter 12. The logarithmizer 11 generates signals which are proportional to the sum of the products of a mass attenuation coefficient and the mass of all substances disposed in the beam path. The output of the converter 12 is supplied to a mean value former and summation circuit 13 which assigns a sliding, weighted mean value to the signals for improving the signal-to-noise ratio. The signals acquired in this manner are stored in two image memories 14 and 15, which are connected to a subtractor 16. The output of the subtractor 16 is supplied to the switching stage 7 via digital contrast enhancement stage 17, such as a window amplifier, a delogarithmizer 18, and a digital-to-analog converter 19. The switching stage 7 directs the signals to a further television monitor 21 for display. The subtraction images can be permanently retained using a permanent image recorder 22, such as a photography device or other type of image pick-up unit.

A control unit 23 controls the entry of successive images into the memories 14 and 15 in such a manner that chronologically successive images are alternately entered into the memories 14 and 15, and overwrite the respective memory contents. Continuous reproduction of a differential image in real time accordingly ensues on the monitor 21.

The installation explained thus far corresponds to that described in U.S. Pat. No. 4,483,342.

In accordance with the principles of the present invention, the patient support table 3 is mounted so as to be vibratable, and is connected to a mechanical oscillator 25, i.e., vibration generator, which is controlled by the control unit 23. The patient 4 on the table 3, or a selected region thereof corresponding to the region being irradiated by the x-ray source 1, is placed in vibration during exposure of the patient for obtaining the above-described differential images. The frequency of the mechanical vibrations may be the same as the image pick-up frequency of the video camera 6, or may differ therefrom such as being half of that image frequency. Body parts which are different in terms of their mechanical properties (i.e., different mass moments of inertia) vibrate with different amplitudes and phases. Gallstones, for example, have a higher mass moment of inertia (i.e., a resistance to the mechanical vibration) than the surrounding tissue. The surrounding tissue will thus more closely "follow" the mechanical vibration and will thus occupy substantially the same position from image-to-image, so that when the successive images are subtracted, this surrounding tissue will be removed form the resulting image. Since the gallstones resist the vibration, their position in successive images will not be the same, and thus the gallstones, or at least the borders thereof, will clearly appear in the resulting image. Calculi in an organ will usually deviate particularly clearly from the surrounding tissue in terms of their vibrational behavior, and will therefore have especially clear borders on the displayed image.

The frequency relation discussed above is only by way of example. The frequencies will be selected based on the mechanical properties of the body part to be imaged in order to achieve the best imaging properties.

The amplitude and frequency of the mechanical vibration of the support table 3, and thus of the patient 4, can be set at a control console 24, by which the entire installation is controlled and monitored.

The above-described image subtraction technique is only one possibility of portraying body parts having different mechanical vibrational behavior. It is also possible to achieve similar results using selective filtering.

In order to portray vessels of the patient 4, a contrast agent injector 26 is mounted at the patient support table 3. The contrast agent injector 26 is also controlled by the control unit 23. The control unit 23 is operated such that the contrast agent injector 26 intermittently injects contrast agent into the corresponding vessel. The injection frquency is matched to the image pick-up frequency, or may differ therefrom, and is also set at the control console 24.

Due to the advance of the contrast agent column in the vessel, the column being interrupted at uniform intervals, the density in the body part under examination fluctuates at a frequency determined, for a given interruption frequency, by the blood vessel flow rate. As a result of the subsequent processing with the above-described image subtraction technique, the blood vessels will appear as a path of alternating dark and light sections and thus be made clearer on the displayed images. This occurs continuously without masks having to be entered into the image memories 14 and 15.

The contrast agent injector 26 may be a double syringe injector wherein two syringes are connected to a common distributor, which leads to the patient. One of the syringes contains contrast agent, and the other syringe contains another liquid, and the syringes are operated in alternation so that the stream of liquid injected into the patient has portions with and without contrast agent following in alternating succession. The contrast agent injector 26 may also be a single syringe which is operated to inject contrast agent into the blood vessel at intervals, thereby producing an image of the blood vessel having sections with and without contrast agent, again following each other in alternating succession.

It is also within the framework of the present invention to use image pick-up systems other than the type shown in the exemplary embodiment. An ultrasound image pick-up system, for example, may be used for image production instead of the image intensifier/video chain.

Although modifications and changes may be suggested by those skilled in the art it is the intention of the inventors to embody within the patent warranted hereon all changes and modifications as reasonably and properly come within the scope of their contribution to the art.

We claim as our invention:

1. A medical examination installation for examining a patient comprising:

means for generating an examination field during an exposure time in which at least a portion of said patient is disposed;

means adapted for mechanically vibrating at least said portion of said patient during said exposure time;

means for detecting said field attenuated by said portion of said patient; and means connected to said means for detecting for generating a visual image of said portion of said patient including means for generating differential images from chronologically successive signals supplied from said means for detecting; wherein said visual image is enhanced as a result of said mechanical vibration.

2. An installation as claimed in claim 1, wherein said means for generating a visual image operates at an image pick-up frequency, and wherein said means for vibrating at least said portion of said patient is a means for vibrating said portion of said patient at a frequency equal to said image pick-up frequency.

3. An installation as claimed in claim 1, wherein said means for generating a visual image operates at an image pick-up frequency, and wherein said means for vibrating at least said portion of said patient is a means for vibrating said portion of said patient at a frequency differing from said image pick-up frequency.

4. An installation as claimed in claim 1, wherein said means for vibrating at least a portion of said patient comprises:

a support table adapted for a patient to lie upon and mounted so as to be mechanically vibrateable; and a mechanical oscillator mechanically connected to said patient support table.

5. An installation as claimed in claim 1, wherein said means for mechanically vibrating a portion of said patient vibrates said portion of said patient at an amplitude and frequency, and wherein said installation further comprises means for adjusting said amplitude and said frequency of said mechanical vibrations.

6. An installation as claimed in claim 1, wherein said means for generating a visual image of said portion of said patient is an image intensifier/video chain.

7. An installation as claimed in claim 1, wherein said means for generating an examination field is a source of x-rays.

8. A method for examining a patient comprising the steps of:

placing at least a portion of said patient in an examination field for an exposure time;

detecting said examination field attenuated by said patient;

mechanically vibrating at least said portion of said patient in said examination field during said exposure time;

generating differential images of said portion of said patient during said exposure time from chronologically successive signals obtained from said means for detecting; and forming a visual image using said differential images, said visual image being enhanced as a result of the step of mechanically vibrating.

* * * * *